(12) United States Patent
Biedermann et al.

(10) Patent No.: US 9,597,120 B2
(45) Date of Patent: Mar. 21, 2017

(54) BONE ANCHORING DEVICE (75) Inventors: Lutz Biedermann, VS-Villingen (DE);
Wilfried Matthis, Weisweil (DE);
Tobias Hägle, Donaueschingen (DE)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 80 days.

(21) Appl. No.: 13/324,616

(22) Filed: Dec. 13, 2011

(65) Prior Publication Data
US 2012/0185003 A1 Jul. 19, 2012

Related U.S. Application Data (60) Provisional application No. 61/422,538, filed on Dec. 13, 2010.

(30) Foreign Application Priority Data

Dec. 13, 2010 (EP) .................................... 10194787

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/7035* (2013.01);
(Continued)

(58) Field of Classification Search
CPC ............ A61B 17/7032; A61B 17/7035; A61B 17/7037; A61B 17/7038; A61B 17/8605
(Continued)

(56) References Cited

U.S. PATENT DOCUMENTS

| 6,736,820 B2 * | 5/2004 | Biedermann et al. ........ 606/308 |
| 7,678,137 B2 * | 3/2010 | Butler et al. .................. 606/246 |

(Continued)

FOREIGN PATENT DOCUMENTS

| JP | 2007-516808 A | 6/2007 |
| JP | 2010-515552 A | 5/2010 |

(Continued)

OTHER PUBLICATIONS

Partial European Search Report for European Application No. EP 10 19 4787.7, Partial European Search Report dated Apr. 1, 2011 and mailed Apr. 11, 2011 (7 pgs.).

(Continued)

*Primary Examiner* — Andrew Yang
(74) *Attorney, Agent, or Firm* — Lewis Roca Rothgerber Christie LLP (57) ABSTRACT

A bone anchoring device includes a bone anchoring element having a head and a shaft, a receiving part for coupling the bone anchoring element to a stabilization element, the receiving part having a bore having a bore axis, a seat member configured to be arranged in the bore and to be rotatable around the bore axis, the seat member forming a seat for polyaxially holding the head, the seat member being configured to allow a greater pivot angle of the bone anchoring element in a first direction compared to other directions when the bone anchoring element and the seat member are in the receiving part, and a pressure member configured to contact the head to exert pressure onto the head, and to be connected to the seat member, such that the pressure member is rotatable together with the seat member around the bore axis.

19 Claims, 6 Drawing Sheets (52) U.S. Cl.
CPC ...... *A61B 17/7038* (2013.01); *A61B 17/8605* (2013.01); *Y10T 29/49826* (2015.01)

(58) Field of Classification Search
USPC ........ 606/264–270, 272, 287, 288, 305–308, 606/319, 320, 328, 278
See application file for complete search history.

(56) References Cited

U.S. PATENT DOCUMENTS

| | | | |
|---|---|---|---|
| 8,021,397 B2 * | 9/2011 | Farris et al. | 606/269 |
| 8,092,494 B2 * | 1/2012 | Butler et al. | 606/246 |
| 8,100,946 B2 * | 1/2012 | Strausbaugh et al. | 606/266 |
| 8,337,530 B2 * | 12/2012 | Hestad et al. | 606/279 |
| 8,409,260 B2 * | 4/2013 | Biedermann et al. | 606/301 |
| 8,419,778 B2 * | 4/2013 | Barry | 606/308 |
| 2004/0153077 A1 * | 8/2004 | Biedermann et al. | 606/73 |
| 2005/0038430 A1 * | 2/2005 | McKinley | 606/61 |
| 2005/0080415 A1 * | 4/2005 | Keyer et al. | 606/61 |
| 2005/0154391 A1 * | 7/2005 | Doherty et al. | 606/61 |
| 2005/0159750 A1 * | 7/2005 | Doherty | 606/73 |
| 2007/0118123 A1 * | 5/2007 | Strausbaugh et al. | 606/61 |
| 2007/0270842 A1 | 11/2007 | Bankoski et al. | |
| 2008/0021473 A1 * | 1/2008 | Butler et al. | 606/63 |
| 2008/0177260 A1 * | 7/2008 | McKinley et al. | 606/60 |
| 2009/0198280 A1 * | 8/2009 | Spratt et al. | 606/267 |
| 2010/0145394 A1 * | 6/2010 | Harvey et al. | 606/302 |
| 2010/0152787 A1 | 6/2010 | Walsh et al. | |
| 2010/0204735 A1 * | 8/2010 | Gephart et al. | 606/264 |
| 2010/0298891 A1 | 11/2010 | Jackson | |
| 2011/0125195 A1 * | 5/2011 | Biedermann et al. | 606/305 |
| 2012/0041495 A9 * | 2/2012 | Biedermann et al. | 606/305 |
| 2012/0109218 A1 * | 5/2012 | Farris | 606/305 |
| 2012/0232598 A1 * | 9/2012 | Hestad et al. | 606/305 |
| 2013/0096623 A1 * | 4/2013 | Biedermann et al. | 606/279 |
| 2013/0110178 A1 * | 5/2013 | Biedermann et al. | 606/305 |
| 2013/0150904 A1 * | 6/2013 | Biedermann et al. | 606/328 |

FOREIGN PATENT DOCUMENTS

| | | |
|---|---|---|
| WO | WO 2005/065397 A2 | 7/2005 |
| WO | WO 2008/089096 A2 | 7/2008 |

OTHER PUBLICATIONS

European Search Report for European Application No. EP 10 19 4787.7, European Search Report dated Jun. 22, 2011 and mailed Jun. 29, 2011 (12 pgs.).

* cited by examiner

BONE ANCHORING DEVICE

CROSS-REFERENCE TO RELATED APPLICATION(S)

The present application claims the benefit of U.S. Provisional Patent Application Ser. No. 61/422,538, filed Dec. 13, 2010, the contents of which are hereby incorporated by reference in their entirety, and claims priority to European Patent Application EP 10 194 787.7, filed Dec. 13, 2010, the contents of which are hereby incorporated by reference in their entirety.

BACKGROUND

Field of the Invention

The invention relates to a bone anchoring device which includes a bone anchoring element for anchoring in a bone or a vertebra and a receiving part for coupling the bone anchoring element to a stabilization element such as a spinal rod, where the bone anchoring element is pivotable in the receiving part and can be pivoted to at least one side with an enlarged pivot angle.

Description of Related Art

A bone anchoring device of this type is described in U.S. Pat. No. 6,736,820. The bone anchoring device includes a bone screw and a receiving part with an open first bore and a substantially U-shaped cross-section for receiving the rod and a second bore on the end opposite to the first bore and a seat for the head. In order that the screw member can be pivoted to at least one side by an enlarged angle, the edge bounding the free end of the second bore is of asymmetric construction. In a modified embodiment an insert piece is provided, which has a spherical bottom as the seat for the head. This allows to change the orientation of the enlarged pivot angle.

US 2005/0154391 A1 describes a bone anchor assembly with a bone anchor and a receiving member. The receiving member has a first section having a first bore defining a first bore axis and a second section having a second bore defining a second bore axis and being sized to receive at least a portion of the bone anchor, wherein the second bore axis intersects the first bore axis. The second section is rotatable about the first bore axis. In an embodiment, the second section is seated internally within the first section.

Since the second section is rotatable with respect to the first section, it is possible to pivot bone anchors out of alignment with one another to avoid interference due to the close proximity of adjacent vertebrae.

Another polyaxial bone anchor is described in US 2007/0118123 A1, wherein a locking element is provided, which is shaped and configured to allow an anchoring member such as a screw or a hook to polyaxially rotate at large angles about a central axis of the bone anchor before compression locking the anchoring member within an anchor head.

SUMMARY

With the bone anchoring devices mentioned above, it may be difficult to adjust a position in which a bone anchoring element has an enlarged pivot angle once the bone anchoring element is partly or fully inserted into a bone.

It is an object of embodiments of the invention to provide an improved bone anchoring device that facilitates adjustment of a direction of an enlarged pivot angle of the bone anchoring element.

A bone anchoring device according to an embodiment of the invention allows rotation of a seat member that holds a head of a bone anchoring element by means of, for example, a driver or tool inserted from a top end of the receiving part, so that a direction of pivoting can be adjusted to any desired direction. The orientation of the driver, for example, the orientation of a handle of the driver, can be used as a precise indicator of the orientation of the seat member. Hence, it is possible or easier to adjust the direction of an enlarged pivot angle during surgery.

Some embodiments may provide a way to pre-adjust the orientation of the seat member using a single support block that fixes the seat member, and then rotating the receiving part relative to the seat member.

The locking of the head in the seat member is effected by pressure exerted from above onto the head, which is then pressed against the seat. Therefore, the locking of the head can be effected in a safe and predictable manner.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
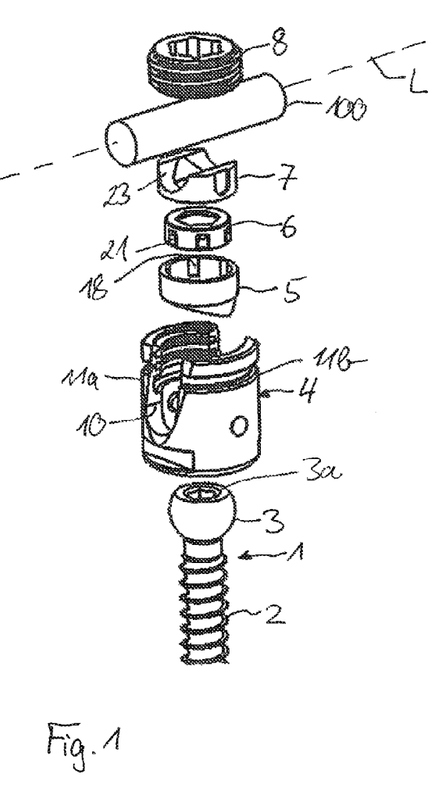
FIG. 1 shows a perspective exploded view of a bone anchoring device with a spinal rod according to an embodiment of the invention.
Figure 2:
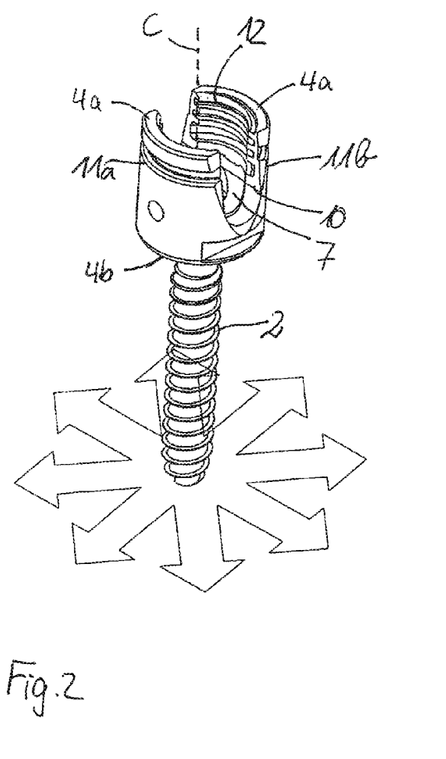
FIG. 2 shows the bone anchoring device of FIG. 1 in an assembled state without a rod or a fixation screw.

As shown in FIGS. 1 and 2, a bone anchoring device according to an embodiment of the invention includes a bone anchoring element 1 in the form of a bone screw having a threaded shaft 2 and a head 3. The head 3 is typically spherically-shaped and has a recess 3a for engagement with a driver or tool. The head 3 can be held in a receiving part 4 that couples the bone anchoring element 1 to a stabilization rod 100. In the receiving part 4, a seat member 5 for providing a seat for the head 3, a first pressure member 6, and a second pressure member 7 for exerting pressure onto the head 3 may be arranged. Further, a fixation element in the form of, for example, a fixation screw 8 is provided for securing and fixing the rod 100 in the receiving part 4. When the bone anchoring device is assembled but an angular position of the bone anchoring element 1 relative to receiving part 4 is not yet fixed, the bone anchoring element 1 can pivot with an enlarged pivot angle in an unlimited number of directions, as shown by the arrows in FIG. 2, depending on a position of the seat member 5 within the receiving part 4.

The receiving part 4 will be described with reference to FIGS. 1 to 4. The receiving part 4 has a top end 4a and a bottom end 4b, a central axis C, and a coaxial bore 9 extending from the top end 4a to the bottom end 4b. Adjacent to the top end 4a, a substantially U-shaped recess 10 is provided, which forms a channel for receiving the rod 100. By means of the recess 10, two free legs 11a, 11b are formed, which may be provided with an internal thread 12 for cooperating with the fixation screw 8. At the lower portion of the bore 9 near the bottom end 4b, a stop 13 in the form of an annular edge is provided for preventing the seat member 5 from escaping through an opening 14 at the bottom end 4b. It shall be noted that the bore 9 is not restricted to the specific shape of the bore shown in the drawings, but can, for example, have different portions with different diameters.

Figure 5:
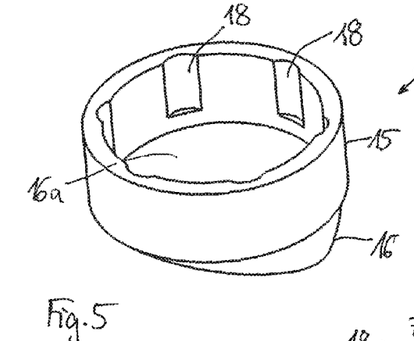
FIG. 5 shows a perspective view of a seat member of the bone anchoring device according to an embodiment of the invention.
Figure 6:
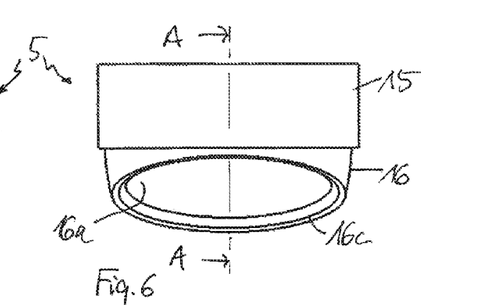
FIG. 6 shows a side view of the seat member of FIG. 5.
Figure 7:
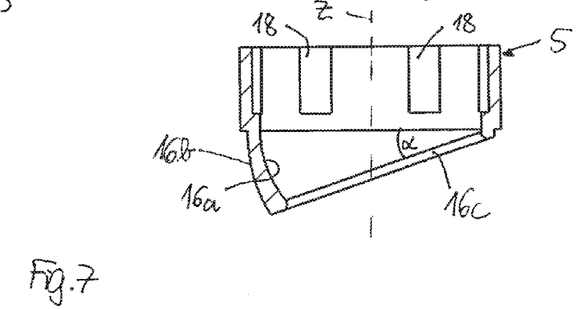
FIG. 7 shows a cross-sectional view of the seat member of FIGS. 5 and 6, the section being taken along line A-A in FIG. 6.
Figure 8:
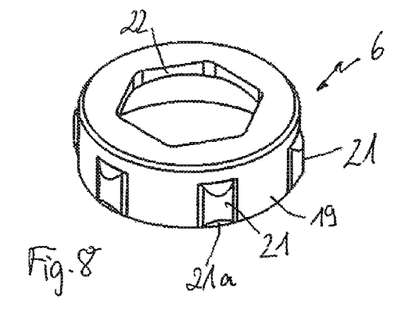
FIG. 8 shows a perspective view of a first pressure member of the bone anchoring device according to an embodiment of the invention.
Figure 9:
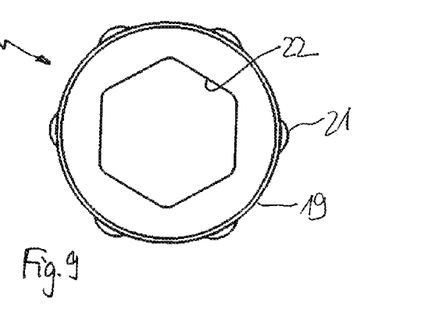
FIG. 9 shows a top view of the first pressure member of FIG. 8.
Figure 10:
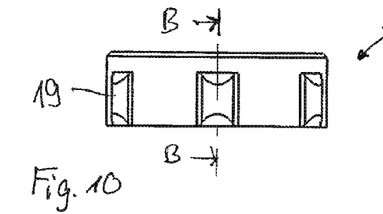
FIG. 10 shows a side view of the first pressure member of FIG. 8.
Figure 11:
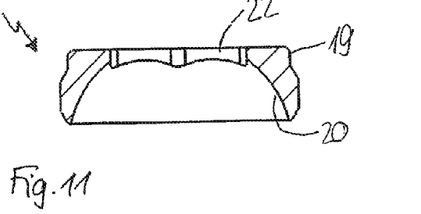
FIG. 11 shows a cross-sectional view of the first pressure member of FIGS. 8-10 along line B-B of FIG. 10.

The seat member 5 is shown in particular in FIGS. 5 to 7. The seat member 5 has a hollow cylindrical first portion 15, an inner diameter of which is slightly larger than a maximum diameter of the spherically-shaped head 3, and an outer diameter of which is slightly smaller than an inner diameter of the bore 9, so that the seat member 5 is insertable into the bore 9. An axial length of the first portion 15 is such that when the head 3 rests within a seat portion 16, the first portion 15 may project above the head 3. Adjacent the first portion 15, the seat member 5 has a hollow second portion 16, which has an internal spherically-shaped surface 16a for providing a seat for the spherically-shaped head 3. An outer surface 16b of the second portion 16 is also spherically-shaped, with an outer diameter that is smaller than the outer diameter of the hollow cylindrical first portion 15.

As can be seen in particular in FIG. 7, the second portion 16 is asymmetric with respect to a plane including a cylinder axis Z. Here, a lower edge 16c is inclined with respect to the hollow cylindrical first portion 15 at an angle $\alpha$. By means of this, the bone anchoring element 1 can pivot at a greater angle to one side or direction relative to the cylinder axis 2, as compared to other sides or directions, when the bone anchoring element 1 is seated in the seat 16a. It shall be noted that the seat member 5 can be sized such that a pivot angle of the bone anchoring element 1 with respect to one side can be as little as approximately 10°, while being as much as approximately 40° to 50° towards an opposite side. At the same time, the size of the pivot angle is limited to the extent that the head 3 still has adequate support in the seat member 5. The second portion 16 is not limited to the design shown. For example, the asymmetry can be formed by a cut-out in a hollow spherical-shaped portion, allowing the shank to pivot only through the cut-out. The inner surface 16a is shown as being a spherically-shaped surface. However, the inner surface can have other shapes, such as, for example, any tapering shape, which is sized so as to prevent the head 3 from falling out.

The seat member 5 may also have a plurality of coaxial recesses 18 on the inner wall of the first portion 15, which open to the free end of the first portion 15 and end at a distance from the lower end of the first portion 15. The recesses 18 are provided to create a form locking engagement with corresponding projections on the first pressure element 6. The number and shape of the recesses 18 is not limited to the number and shape of the recesses shown in the figures. For example, only one recess is necessary for a form lock connection between the first pressure element 6 and the seat member 5.

Figure 3:
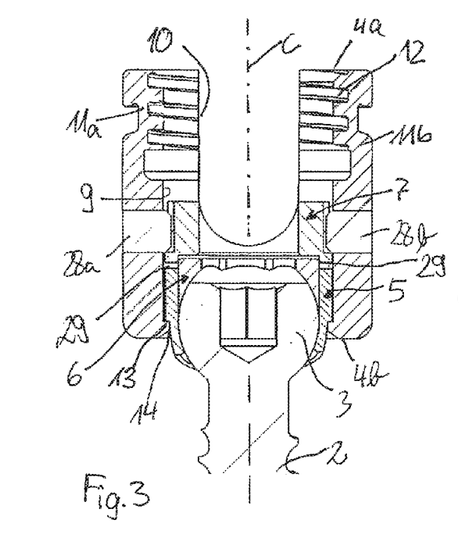
FIG. 3 shows a cross-sectional view of the bone anchoring device of FIG. 1, the section being taken perpendicular to a rod axis.
Figure 4:
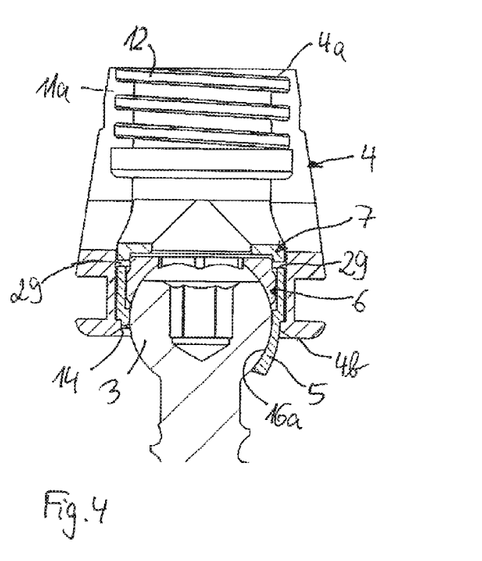
FIG. 4 shows a cross-sectional view of the bone anchoring device of FIG. 1, the section being taken along the rod axis.

As can be seen in particular in FIGS. 3 and 4, the seat member 5 abuts on or against the annular edge 13 of the receiving part 4, when the seat member 5 is inserted into the receiving part 4 and moved downward along or through the bore 9. At least a portion of the second portion 16 of the seat member 5 extends out of the lower opening 14 of the receiving part 4. The seat member 5 is rotatable within the receiving part 4, so that the inclined edge 16c can assume any position relative to the U-shaped recess 10. As a consequence, the position with the enlarged pivot angle for the anchoring element 1 can assume any orientation with respect to the U-shaped recess 10, and therefore also with respect to the rod axis L.

The first pressure member 6 will now be explained, specifically with reference to FIGS. 8 to 11. The first pressure member 6 has a substantially hollow cylindrical portion 19, an outer diameter of which is only slightly smaller than the inner diameter of the first hollow cylindrical portion 15 of the seat member 5, so that, as can be seen in FIGS. 3 and 4, the first pressure member 6 can be inserted into the first portion 15 of the seat member 5 and is axially movable with respect to the seat member 5. On a side configured to face the head 3, the first pressure member 6 has a recess 20, which in this embodiment is a spherically-shaped recess with an inner diameter adapted to the diameter of the head 3, so that the first pressure member 6 can exert pressure onto the head 3. When the first pressure member 6 is inserted into receiving part 4, the first pressure member 6 rests on the head 3. The first pressure member 6 has an axial length such that it projects above the seat member 5 in this position, as can be seen in FIGS. 3 and 4. At an outer surface of the cylindrical portion 19, a plurality of coaxially extending projections 21 are provided to engage the recesses 18 of the seat member 5, to form a form locking connection between the first pressure member 6 and the seat member 5. The recesses 18 at the seat member 5 also form guides for axial movement of the first pressure member 6. In other embodiments, instead of the plurality of recesses and projections at the inner surface of the seat member and the outer surface of the first pressure member, respectively, any other connection between the seat member and the first pressure member which allows the transmission of rotational forces from the first pressure member to the seat member can be employed. The projections 21 end at a distance from a top end of the first pressure member 6 and can have a chamfer 21a to facilitate engagement with corresponding recesses 18 of the seat member 5.

On an end opposite to the recess 20, the first pressure member 6 includes an engagement structure 22 for engagement with a driver or tool. In the embodiment shown, the engagement structure 22 is a hexagonal recess.

Figure 12:
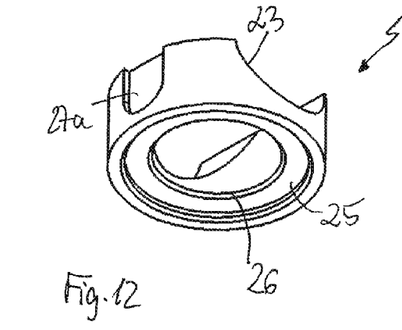
FIG. 12 shows a perspective view of a second pressure member of the bone anchoring device from below, according to an embodiment of the invention.
Figure 13:
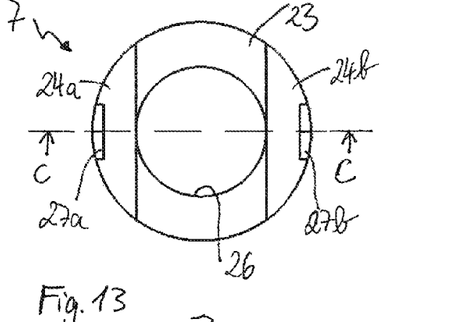
FIG. 13 shows a top view of the second pressure member of FIG. 12.
Figure 14:
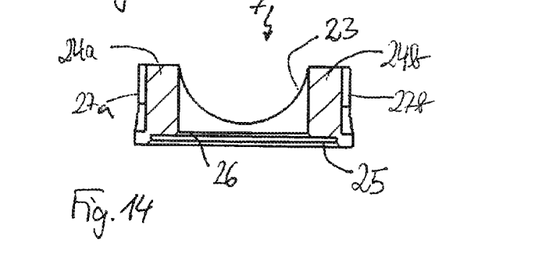
FIG. 14 shows a cross-sectional view of the second pressure member of FIGS. 12 and 13 along line C-C of FIG. 13.

The second pressure member 7 will be explained with reference to FIGS. 12 to 14. The second pressure member 7 is substantially cylindrical, and has on a side configured to be opposite to the head 3 a cylindrically-shaped recess 23, which is sized so as to guide the rod 100 therein. By means of the recess 23 two legs 24a, 24b are formed. On a side opposite to the recess 23, the second pressure member 7 has a coaxial recess 25, which is sized such that the second pressure member 7 can rest on the cylindrical portion 19 of the first pressure member 6. The second pressure member 7 also has a shallow coaxial bore 26 to allow access to the first pressure member 6 with a driver or tool. On an outer sidewall of the legs 24a, 24b, two coaxial recesses 27a, 27b are formed, which are open to a top side and closed to a bottom side of the second pressure member 7, by means of which the second pressure member 7 can be prevented from rotating and/or from escaping through the top end 4a of the receiving part 4, for example, by means of pins 28a, 28b provided at the receiving part 4 as shown in FIG. 3.

When the second pressure member 7 is inserted into receiving part 4, the second pressure member 7 abuts on or against the first pressure member 6 in such a way that there is a gap 29 between the seat member 5 and the second pressure member 7, so that the second pressure member 7 does not directly press onto the seat member 5.

Figure 15:
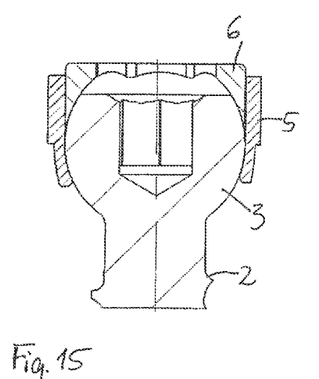
FIG. 15 shows a cross-sectional view of a bone anchoring element, a seat member and a first pressure member according to an embodiment of the invention.
Figure 16:
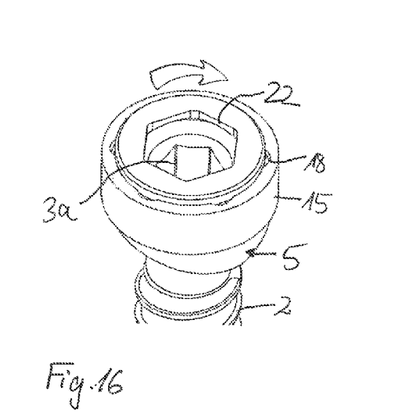
FIG. 16 shows a perspective view of an assembly including the bone anchoring element, the seat member and the first pressure member as seen in FIG. 15.

As shown in FIGS. 15 and 16, the form lock connection between the first pressure member 6 and the seat member 5 allows transmission of a rotational force exerted by a driver or tool, which engages the first pressure member 6 at the recess 22, to the seat member 5, so that the seat member 5 rotates with the first pressure member 6. Since the form lock connection between the first pressure member 6 and the seat member 5 is such that the first pressure member 6 can slide in an axial direction with respect to the seat member 5, the second pressure member 7 can exert pressure onto the first pressure member 6 to press the head 3 against the seat member 5.

The bone anchoring device, as a whole or in part, is made of a bio-compatible material, for example, a bio-compatible metal, such as titanium or stainless steel, bio-compatible alloys such as nitinol or others, or bio-compatible plastic materials, such as for example, medical grade polyetheretherketone (PEEK). Parts of the bone anchoring device can be made of the same material or can be made of different materials.

Figure 17A:
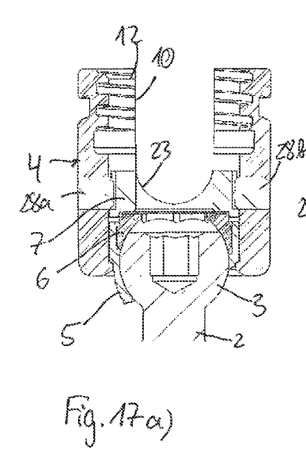
FIGS. 17*a* to 17*c* show steps of use of the bone anchoring device according to the first embodiment.
Figure 17B:
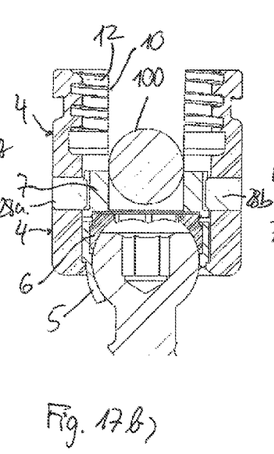
Figure 17C:
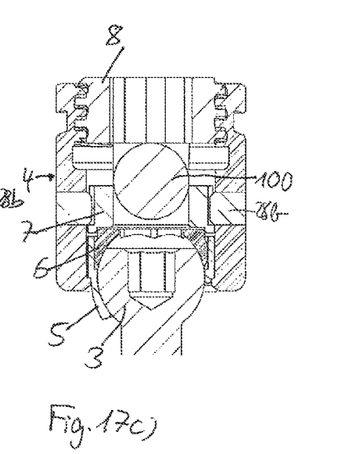

The steps of use of the bone anchoring device are shown in FIGS. 17a-17c. The bone anchoring device may be pre-assembled in such a way that the seat member 5, the bone anchoring element 1, the first pressure member 6 and the second pressure member 7 are inserted into the receiving part 4, and secured against falling out, as well as against rotation of the second pressure member 7, for example, by means of pins 28a, 28b. In this condition, the cylindrically-shaped recess 23 of the second pressure member 7 is aligned with the U-shaped recess 12 of the receiving part 4. The seat member 5 abuts on or against the annular edge 13 of the receiving part 4. In the pre-assembled state, the head 3 can freely pivot within the seat member 5. In a next step, the bone anchoring element 1 is screwed or otherwise inserted into a bone or a vertebra. Usually a plurality of bone anchoring elements 1 are used and connected to the rod 100. Before insertion of the rod 100, the receiving parts 4 are aligned through pivoting the receiving parts 4 relative to their corresponding heads 3. To adjust the position of the seat member 5 in view of the desired direction with the enlarged pivot angle, the first pressure member 6 is rotated with a driver or tool. Since the seat member 5 is positively connected to the first pressure member 6, the seat member 5 rotates with the first pressure member 6. Then, as shown in FIG. 17b, the rod 100 is inserted. Next, as shown in FIG. 17c the fixation screw 8 is screwed in between the legs 11a, 11b of the receiving part 4 and tightened so that the rod 100 presses onto the second pressure member 7, which itself presses onto the first pressure member 6, thereby locking the head 3 relative to the seat member 5. Simultaneously, the seat member 5 is pressed against the annular edge 13, and is thereby also fixed in its rotational position.

Modifications of the embodiments are conceivable. For example, it is possible to omit the second pressure member, and to press directly with the rod onto the first pressure member. In a further modification, the second pressure member has legs which extend above an inserted rod, while the fixation element may be a two-part fixation element, with an outer screw acting on the second pressure element and an inner screw acting on the rod. In a further modification, various different kinds of bone anchors can be used for the bone anchoring element, such as bone nails, other types of bone screws, canulated screws, etc. In addition, the head and the shaft of the bone anchoring element may be separate parts that are connectable to each other.

Figure 18A:
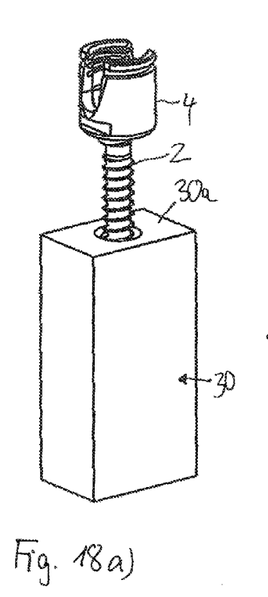
FIGS. 18a to 18c show steps of adjusting the seat member relative to the receiving part according to a first exemplary embodiment.
Figure 18B:
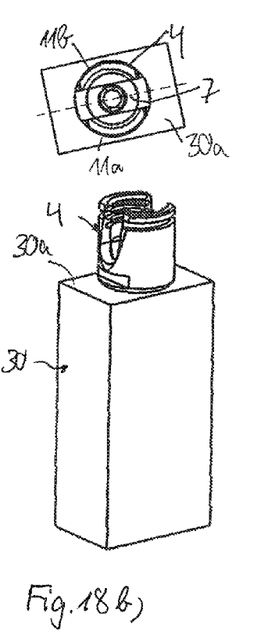
Figure 18C:
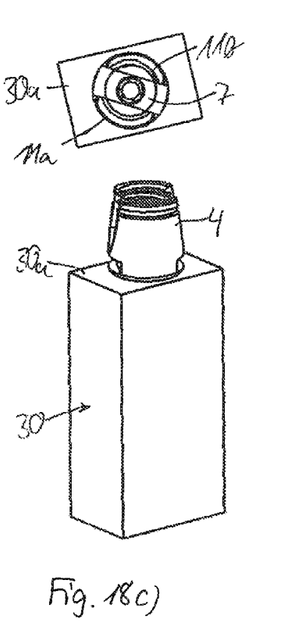
Figures 19, 20:
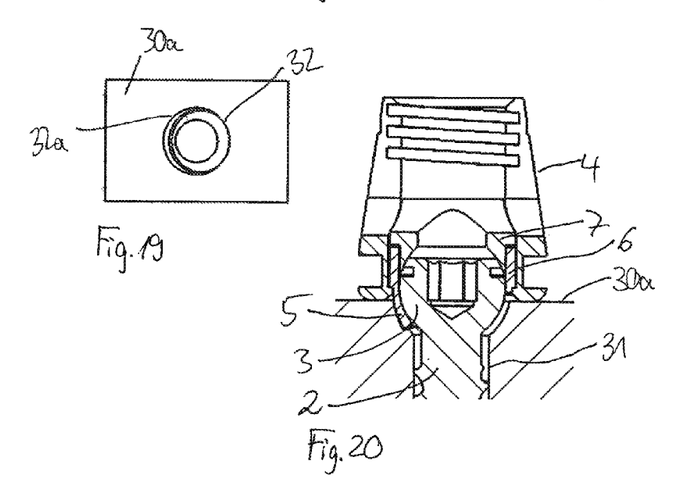
FIG. 19 shows a top view of a support block for adjusting the seat member relative to the receiving part as shown in FIGS. 18a-18c.
FIG. 20 shows a cross-sectional view of the support block of FIGS. 18a-18c, with a bone anchoring device inserted, the section being taken along a rod axis.

FIGS. 18a to 20 show an example of a tool and a method for adjusting a rotational position of the seat member 5. A support block 30 is provided which has a longitudinal bore 31 extending from a top surface 30a into the support block 30. In the top surface 30a, a recess 32 is formed that extends into the support block 30, the recess 32 having an inner surface 32a corresponding to the outer surface 16b of the second portion 16 of the seat member 5. Hence, the recess 32 is asymmetrical and adapted to the shape of the lower portion 16 of the seat member 5. As shown in FIGS. 19 and 20, when the pre-assembled bone anchoring device is inserted with the threaded shaft 2 into the hole 31, the second portion 16 of the seat member 5 rests in the recess 32 and is prevented from rotating therein due to the form lock or matching connection.

Once the bone anchoring device is fully inserted in the bore 31, the bone anchoring element 1 and/or the receiving part 4 including the second pressure member 7 may be rotatable with respect to the seat member 5 and the first pressure member 6. Hence, the receiving part 4 can be rotated with respect to the seat member 5 and the first pressure member 6, so that the enlarged pivot angle of the seat member 5 has a desired orientation. Two examples with different orientations are shown in FIGS. 18b and 18c.

Figures 21, 22, 23:
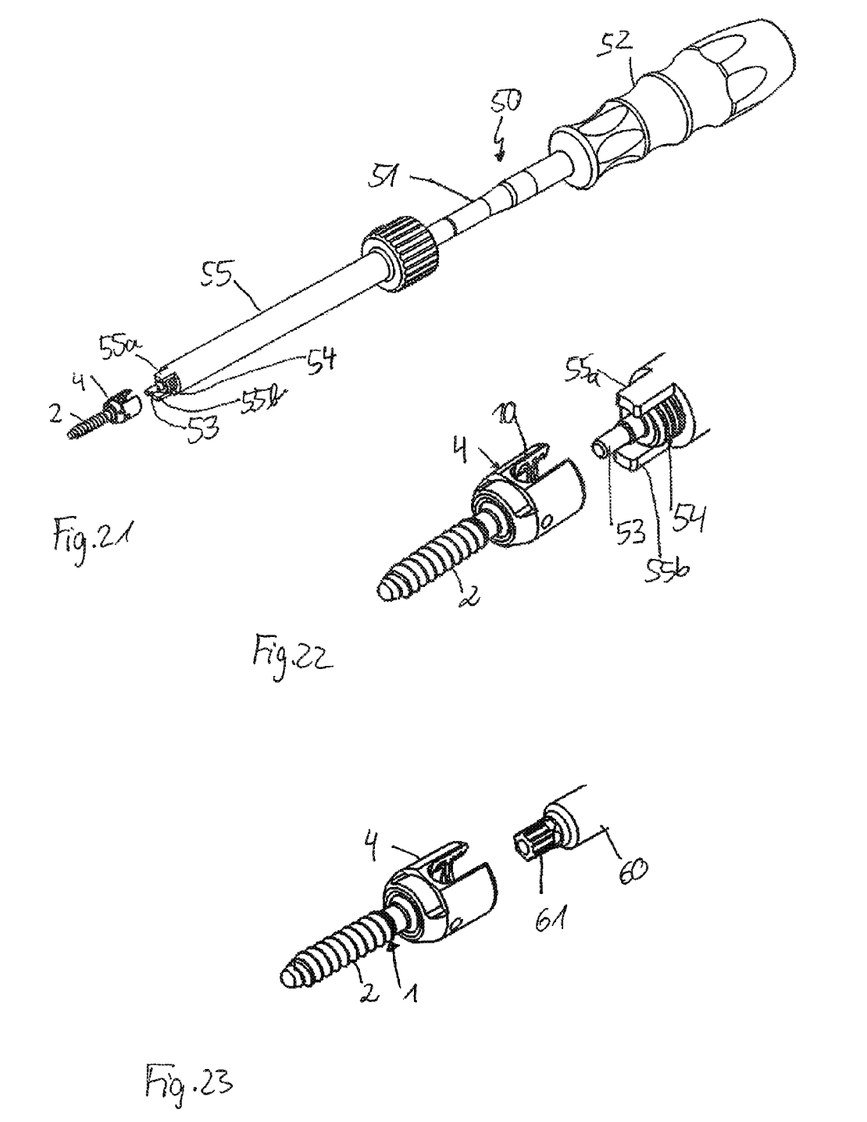
FIG. 21 shows a perspective view of a bone anchoring device with an insertion tool according to an embodiment of the invention.
FIG. 22 shows an enlarged portion of the device of FIG. 21.
FIG. 23 shows a perspective view of a bone anchoring device and a portion of another embodiment of an insertion tool.

Adjustments using the support block 30 can be made before an actual surgery or procedure takes place, and can serve for adjusting or setting a pre-orientation of the seat member 5. For holding a preselected orientation of the seat member 5, an insertion tool for inserting the bone anchoring element 1 into the bone can be used, which is shown in FIGS. 21 and 22. Insertion tool 50 has a first portion 51 with a handle 52 at one end, a tip 53 at the other end, and adjacent to the tip 53, an externally threaded portion 54 for cooperating with the internal thread 12 on the legs 11a, 11b of the receiving part 4. The tool further has a second portion 55 with two side flanges 55a, 55b for engaging the U-shaped recess 10 of the receiving part 4. The first portion Si is rotatable with respect to the second portion 55. When the tool 50 engages the bone anchoring device, the second portion 55 holds the receiving part 4 through engagement with the U-shaped recess, and the tip 53 presses onto the head 3 when the threaded portion 54 is screwed in between the legs 11a, 11b. The orientation of the seat member 5 is thereby secured by the pre-tension created by the tool 50, and the shaft 2 can then be inserted into the bone with the insertion tool 50.

In an alternative method, the bone anchoring device can be inserted into a bone with a tool 60, as shown in FIG. 23, which has a simple drive portion 61 at its end, for example a torx driver. In this case, a rotational orientation of the seat member 5 may not be maintained during insertion into the bone. After insertion of the shaft 2, a separate driver or tool for engagement with the recess 22 of the first pressure member 6 is used to adjust the rotational position of the seat member 5 from the top end.

A visible mark can be provided to serve as an indicator for the particular position of the seat member 5.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
   a bone anchoring element having a head and a shaft configured to be anchored in a bone or a vertebra;
   a receiving part for coupling the bone anchoring element to a stabilization element, the receiving part having a first end, a second end, a bore extending from the first end to the second end and having a bore axis, and a recess extending from the first end towards the second end for receiving the stabilization element, the recess being in communication with the bore;
   a seat member configured to be inserted into the bore from the first end of the receiving part and to be arranged in the bore at the second end of the receiving part, and to be rotatable around the bore axis, the seat member having a first end with an opening for inserting the head and a seat for polyaxially holding the head, the seat member being configured to allow a first pivot angle of the bone anchoring element in a first direction relative to the bore axis that is greater than other pivot angles in other directions relative to the bore axis when the bone anchoring element and the seat member are in the receiving part; and
   a pressure member configured to be connected to the first end of the seat member;
   wherein when the head is held in the seat and central axes of the bone anchoring element and the seat member are coaxial, the first end of the seat member extends farther away from the shaft than the head extends from the shaft; and
   wherein when the pressure member and the seat member are in the receiving part and connected to one another and the head is held in the seat member, the pressure member is configured to contact the head to exert pressure onto the head, and is axially movable but rotationally fixed relative to the seat member, such that the pressure member is rotatable together with the seat member around the bore axis in the receiving part, so as to allow for adjustment of an orientation of the first direction relative to the bore axis.

2. The bone anchoring device of claim 1, wherein when the seat member is in the receiving part, the seat member abuts against a stop in the receiving part.

3. The bone anchoring device of claim 1, wherein the seat member has an at least partially spherical inner surface.

4. The bone anchoring device of claim 1, wherein when the seat member is in the receiving part, the seat member projects at least partly out of the second end of the receiving part in a direction away from the first end of the receiving part.

5. The bone anchoring device of claim 1, wherein the seat member has an inclined lower edge to provide the first pivot angle in the first direction for the bone anchoring element inserted therein.

6. The bone anchoring device of claim 1, wherein the pressure member and the seat member are connectable via a form lock connection.

7. The bone anchoring device of claim 6, wherein the seat member has at least one recess or projection for engaging a corresponding projection or recess at the pressure member.

8. The bone anchoring device of claim 1, wherein the pressure member has an engagement portion for engagement with a driver or tool.

9. The bone anchoring device of claim 8, wherein the engagement portion is provided at a side of the pressure member which faces away from the head when the bone anchoring element, the seat member, and the pressure member are in the receiving part.

10. The bone anchoring device of claim 1, wherein the seat member and the pressure member each comprises a cylindrical portion and an engagement portion, wherein when the respective engagement portions are engaged, the cylindrical portions are configured to be axially movable but rotationally fixed relative to one another.

11. The bone anchoring device of claim 1, wherein the recess for receiving the stabilization element is U-shaped.

12. The bone anchoring device of claim 1 wherein the seat member has a first portion with a greatest outer width of the seat member, and wherein when the pressure member and the seat member are connected to one another, the pressure member is configured to extend into a portion of the seat member with the greatest outer width.

13. A bone anchoring device comprising:
   a bone anchoring element having a head and a shaft configured to be anchored in a bone or a vertebra;
   a receiving part for coupling the bone anchoring element to a stabilization element, the receiving part having a first end, a second end, a bore extending from the first end to the second end and having a bore axis, and a recess extending from the first end towards the second end for receiving the stabilization element, the recess being in communication with the bore;

a seat member configured to be inserted into the bore from the first end of the receiving part and to be arranged in the bore at the second end of the receiving part, and to be rotatable around the bore axis the seat member forming a seat for polyaxially holding the head, the seat member being configured to allow a first pivot angle of the bone anchoring element in a first direction relative to the bore axis that is greater than other pivot angles in other directions relative to the bore axis when the bone anchoring element and the seat member are in the receiving part; and a pressure member configured to be connected to the seat member;

wherein when the pressure member and the seat member are in the receiving part and connected to one another and the head is held in the seat member, the pressure member is configured to contact the head to exert pressure onto the head and is axially movable but rotationally fixed relative to the seat member, such that the pressure member is rotatable together with the seat member around the bore axis in the receiving part, so as to allow for adjustment of an orientation of the first direction relative to the bore axis, and the receiving part is configured to provide an abutment that restricts the bone anchoring element, the seat member, and the pressure member from falling out of the first end of the receiving part.

14. A bone anchoring device comprising:

a bone anchoring element having a head and a shaft configured to be anchored in a bone or a vertebra;

a receiving part for coupling the bone anchoring element to a stabilization element, the receiving part having a first end, a second end, a bore extending from the first end to the second end and having a bore axis, and a recess extending from the first end towards the second end for receiving the stabilization element, the recess being in communication with the bore;

a seat member configured to be inserted into the bore from the first end of the receiving part and to be arranged in the bore at the second end of the receiving part, and to be rotatable around the bore axis, the seat member forming a seat for polyaxially holding the head, the seat member being configured to allow a first pivot angle of the bone anchoring element in a first direction relative to the bore axis that is greater than other pivot angles in other directions relative to the bore axis when the bone anchoring element and the seat member are in the receiving part;

a first pressure member configured to be connected to the seat member and to contact the head to exert pressure onto the head; and a second pressure member configured to be positioned on a side of the first pressure member opposite the head, and defining a recess for guiding the stabilization element;

wherein when the first pressure member, the second pressure member, and the seat member are in the receiving part and connected to one another and the head is held in the seat member, the first pressure member is axially movable but rotationally fixed relative to the seat member, such that the first pressure member is rotatable together with the seat member around the bore axis in the receiving part, so as to allow for adjustment of an orientation of the first direction relative to the bore axis, and the second pressure member has a coaxial bore therethrough to provide access to the first pressure member from the first end of the receiving part.

15. The bone anchoring device of claim 14, wherein the second pressure member is configured to press onto the first pressure member without touching the seat member to lock the head in the seat member.

16. The bone anchoring device of claim 14, wherein the second pressure member is rotatable with respect to the first pressure member when the first pressure member and the second pressure member are engaged in the receiving part.

17. The bone anchoring device of claim 14, wherein the second pressure member is securable against rotation in the receiving part.

18. A method of coupling a stabilization element to a bone via a polyaxial bone anchoring device, the bone anchoring device comprising a bone anchoring element having a head and a shaft configured to be anchored in a bone, a receiving part for coupling the bone anchoring element to the stabilization element, the receiving part having a first end, a second end, a bore extending from the first end to the second end and having a bore axis, and a recess extending from the first end towards the second end for receiving the stabilization element, the recess being in communication with the bore, a seat member configured to be inserted into the bore from the first end of the receiving part and to be arranged in the bore at the second end of the receiving part, and to be rotatable around the bore axis, the seat member having a first end with an opening for inserting the head and a seat for polyaxially holding the head, the seat member being configured to allow a first pivot angle of the bone anchoring element in a first direction relative to the bore axis that is greater than other pivot angles in other directions relative to the bore axis when the bone anchoring element and the seat member are in the receiving part, and a pressure member configured to be connected to the first end of the seat member, wherein when the head is held in the seat and central axes of the bone anchoring element and the seat member are coaxial, the first end of the seat member extends farther away from the shaft than the head extends from the shaft, and wherein when the pressure member and the seat member are in the receiving part and connected to one another and the head is held in the seat member, the pressure member is configured to contact the head to exert pressure onto the head, and is axially movable but rotationally fixed relative to the seat member, such that the pressure member is rotatable together with the seat member around the bore axis in the receiving part, the method comprising:

inserting the bone anchoring device into the bone, the bone anchoring device comprising the receiving part with at least the bone anchoring element and the seat member inserted therein;

connecting the pressure member to the seat member;

rotating the pressure member to rotate the seat member and to adjust an orientation of the first direction relative to the bore axis;

tilting the receiving part relative to the bone anchoring element substantially along the first direction;

inserting the stabilization element into the recess; and advancing a closure element into the recess to push the stabilization element and the pressure member towards the second end of the receiving part, wherein the pressure element is pushed against the head to lock respective positions of the seat member and the bone anchoring element relative to the receiving part.

19. The method of claim 18, wherein prior to inserting the bone anchoring device into the bone, the method further comprises:
  inserting the seat member into the receiving part; and
  inserting the head of the bone anchoring element into the seat member.

* * * * *

UNITED STATES PATENT AND TRADEMARK OFFICE
CERTIFICATE OF CORRECTION

PATENT NO. : 9,597,120 B2
APPLICATION NO. : 13/324616
DATED : March 21, 2017
INVENTOR(S) : Lutz Biedermann et al.

Page 1 of 1

It is certified that error appears in the above-identified patent and that said Letters Patent is hereby corrected as shown below:

In the Specification

Column 4, Line 10    Delete "axis 2,",
                     Insert --axis Z,--

Column 7, Line 15    Delete "portion Si",
                     Insert --portion 51--

In the Claims

Column 8, Line 52,   After "1",
Claim 12             Insert --,--

Column 9, Line 4,    After "axis",
Claim 13             Insert --,--

Signed and Sealed this
Eleventh Day of September, 2018

Andrei Iancu
*Director of the United States Patent and Trademark Office*